United States Patent [19]
Holmes

[11] Patent Number: 6,039,467
[45] Date of Patent: *Mar. 21, 2000

[54] LIGHTING SYSTEM AND METHODS FOR A DISPENSING DEVICE

[75] Inventor: William K. Holmes, San Diego, Calif.

[73] Assignee: Omnicell Technologies, Inc., Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/761,726

[22] Filed: Dec. 5, 1996

[51] Int. Cl.[7] .............................. G06F 17/00; G06F 7/00; G07F 11/00
[52] U.S. Cl. ................................ 364/479.01; 364/479.02; 364/479.06; 364/479.07; 364/479.11; 364/479.12; 364/479.13; 364/479.14; 221/2; 221/3
[58] Field of Search .......................... 364/479.01, 479.11, 364/479.07, 479.06, 479.1, 479.12, 479.14, 479.13; 312/348.3, 223.1, 223.5, 223.6, 223.2; 221/2, 3

[56] References Cited

U.S. PATENT DOCUMENTS

| | | | |
|---|---|---|---|
| Re. 35,743 | 3/1998 | Pearson | 221/2 |
| 3,762,601 | 10/1973 | McLaughlin | 221/2 |
| 3,998,356 | 12/1976 | Christensen | 221/2 |
| 4,071,747 | 1/1978 | Pantanella | 362/127 |
| 4,114,965 | 9/1978 | Oye et al. | 312/209 |
| 4,382,688 | 5/1983 | Machmer | 340/10 |
| 4,473,884 | 9/1984 | Behl | 364/479.12 |
| 4,575,719 | 3/1986 | Bertagna et al. | 340/825.35 |
| 4,626,105 | 12/1986 | Miller | 368/10 |
| 4,640,560 | 2/1987 | Blum | 312/234 |
| 4,691,470 | 9/1987 | Landell et al. | 43/55 |
| 4,717,042 | 1/1988 | McLaughlin | 221/3 |
| 4,803,604 | 2/1989 | Nichols et al. | 362/154 |
| 4,813,753 | 3/1989 | Relyea | 312/291 |
| 5,200,891 | 4/1993 | Kehr et al. | 364/413.01 |
| 5,242,223 | 9/1993 | Koves | 312/348.3 |
| 5,257,693 | 11/1993 | Kwasniak | 312/348.3 |
| 5,292,029 | 3/1994 | Pearson | 221/2 |
| 5,355,289 | 10/1994 | Krenn | 362/253 |
| 5,392,951 | 2/1995 | Gardner et al. | 221/2 |
| 5,408,443 | 4/1995 | Weinberger | 368/10 |
| 5,459,648 | 10/1995 | Courtney | 362/154 |
| 5,661,978 | 9/1997 | Holmes et al. | 62/3.6 |
| 5,664,856 | 9/1997 | Pacetti | 312/348.3 |
| 5,673,983 | 10/1997 | Carlson et al. | 312/218 |
| 5,745,366 | 4/1998 | Higham et al. | 364/479.11 |

FOREIGN PATENT DOCUMENTS

| | | |
|---|---|---|
| 2130252 | 2/1996 | Canada . |
| 2650426 | 5/1991 | France . |
| 4-05147706 | 6/1993 | Japan . |
| 656613 | 4/1979 | U.S.S.R. . |
| WO 95/03587 | 2/1995 | WIPO . |
| WO 96/21925 | 7/1996 | WIPO . |
| WO 98/26746 | 6/1998 | WIPO . |

OTHER PUBLICATIONS

"Burnout: Why Do We Blame the Nurse" Drug ATM's Can Reduce Error Rate. AJN Nov. 1995.
Borel, Jacque et al., "Effect of an automated nursing unit–based drug–dispensing device on medication errors" *Am. J Health–Syst. Pharm* 52:1875–9, 1995.
Product Brochure, Access Automated Drug Control System, Lionvill Systems, Inc., print date Jul. 1993.
Product Brochure, Omnicell See and Touch Supply System, Omnicell Technologies, Inc., 1994.

*Primary Examiner*—William E. Terrell
*Assistant Examiner*—Wonki Park
*Attorney, Agent, or Firm*—Townsend and Townsend and Crew

[57] ABSTRACT

The invention provides an exemplary dispensing unit which includes a cabinet having a plurality of drawers. A plurality of light sources are attached to a bottom of each of the drawers. A liner is removably held within each of the drawers above the light sources. Further, a plurality of adjustable dividers are provided to divide the liner into a plurality of bins for holding items. A processor having a memory for storing a list of items which are held within the bins and an entry device for entering a request for item removal is further provided. A plurality of light indicators are operably attached to the dividers and are arranged such that each light indicator is aligned with a corresponding light source.

27 Claims, 7 Drawing Sheets

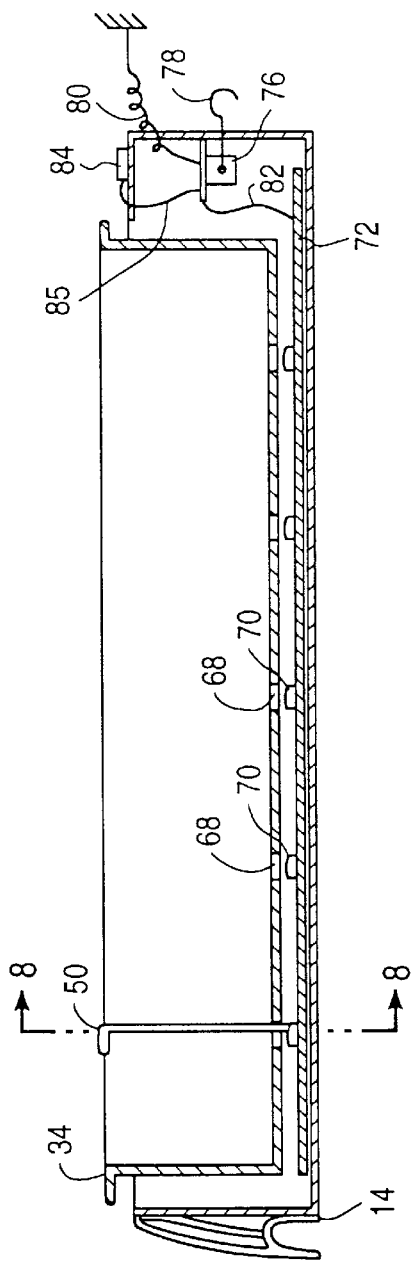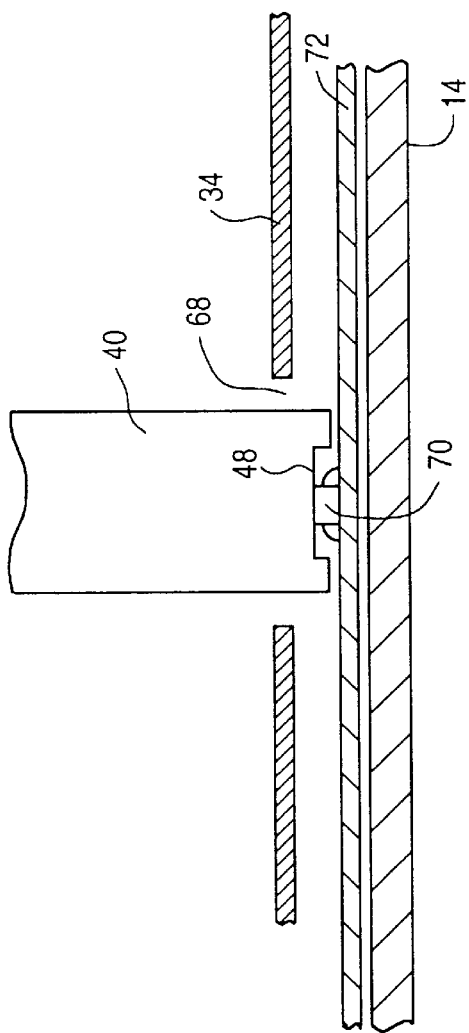

LIGHTING SYSTEM AND METHODS FOR A DISPENSING DEVICE

BACKGROUND OF THE INVENTION

The present invention relates generally to the field of item dispensing, and particularly to the dispensing of items within a medical facility. In one specific aspect, the invention provides a dispensing unit having a lighting system which guides a caregiver to a specific storage bin which holds a selected item.

Traditionally, many large medical facilities maintained essentially all of their medical supplies in a central inventory location. Such an arrangement in many cases proved to be inconvenient because of the large distance between the central inventory location and the patients who used the supplies. To facilitate the delivery of supplies to the patients, some medical facilities have begun to rely on the use of local dispensing stations. Such dispensing stations are placed in the medical facility nearer to the patients and are designed to hold various supplies and pharmaceuticals typically needed by the patients. Such dispensing stations typically have the ability to maintain records on the number and type of items that are both dispensed and restocked. Further, such dispensing stations may be configured to provide different levels of security to the items held therein. For instance, the items may be freely available to any caregiver. Higher levels of security may be provided by including various locks or restrictive devices to prevent access to either the number or type of items to be dispensed.

One particular type of dispensing device which is becoming accepted within the medical industry comprises a cabinet having a plurality of retractable drawers which hold the items. The individual drawers are often divided into bins so that more than one type of item may be held within each drawer. Security may be provided by providing locks on the drawers to allow access to only certain caregivers, certain items and/or certain times of day.

When using such drawers in a secured environment, a number of issues need to be addressed. For example, it would be desirable to provide convenient access to each of the bins, including the ability to quickly locate a bin having a selected item. It would further be desirable to efficiently utilize the space of each drawer so that a maximum number of items could be held within the cabinet. Further, it would be desirable to allow the bins to be arranged in different sizes so that each drawer could be customized depending upon the types of items that are to be stored.

The ability to address some or all of these issues while still providing adequate security is especially challenging. For example, U.S. Pat. No. 5,014,875 describes a dispensing station having a plurality of retractable drawers. To provide security to the items and to assist a caregiver in the location of a selected item, a carousel system is included in the drawers. However, such a system is a gross underutilization of drawer space and is therefore undesirable.

Another issue that needs to be addressed with such dispensing stations is the need to restock dispensed items. Previously proposed methods include individually restocking each bin with a supply cart that is transported throughout the medical facility. However, restocking in this manner is time consuming, thus preventing access to the supplies for long time periods during restocking, and may also lead to inventory restocking errors.

A further consideration in the development of a dispensing station which is divided into a matrix of bins is that of ensuring a user will properly select the correct bin. Recent studies indicate a high incidence of removal errors from such dispensing stations. Healthcare providers are therefore anxious to reduce removal errors which stem from users selecting incorrect items from a tray containing many bins.

It would therefore be desirable to provide systems, methods and apparatus to overcome or greatly reduce these and other problems. It would be particularly desirable if a dispensing system were provided which would provide some level of security to the items while still providing convenient access to the items, including the ability to easily locate a selected item so that removal errors may be reduced. Such a dispensing system should also efficiently utilize the storage space so that large inventories of items or large numbers of items may be held therein. It would be further desirable if such a dispensing system could be tailored to allow for different sized items to be stored therein. Further, it would be desirable if such a system were easy to restock so that time and errors could be reduced when replenishing the dispensed items.

SUMMARY OF THE INVENTION

The invention provides an exemplary dispensing system for dispensing various types of items. Although useful in a wide variety of applications, the dispensing system will find its greatest use in dispensing medical supplies, pharmaceuticals, and the like in medical facilities. In one exemplary embodiment, the dispensing system comprises a cabinet having at least one storage location. A plurality of adjustable dividers are provided to divide the storage location into a plurality of bins. In this way, the number and size of bins may be tailored to accommodate various types of items. A processor is further provided and includes a memory for storing a list of items which are held within the bins as well as an entry device for entering requests for item removal. A plurality of light indicators are operably attached to at least some of the dividers. The light indicators are arranged such that at least one light indicator will uniquely identify one of the bins when lighted. For example, the light indicator may be in the shape of an arrow or other pointer which points to the correct bin. With this arrangement, a caregiver may enter an item removal request into the processor, and the bin having the requested item will be lighted to unambiguously guide the caregiver to the correct bin.

In an alternative aspect, at least two light indicators, which are preferably opposite of each other, may be employed to unambiguously and uniquely identify one of the bins when lighted.

In one exemplary aspect, the cabinet is provided with a plurality of drawers which function as storage locations. A plurality of light sources are provided within each drawer, and a liner is removably held within each drawer above the light sources. With this configuration, the adjustable dividers may be employed to divide the liner into a plurality of bins. When the liner is placed into the drawer, each light indicator is aligned with one of the light sources. In this manner, regardless of the configuration of the dividers, each light indicator will always be aligned with a light source so that any one of the bins may be lighted when selecting an item.

The dividers will preferably be configured so that the bins will be orthogonal in geometry when connected to the liner. Further, the light sources will preferably be arranged in a two dimensional array so that a light indicator will always be aligned with one of the light sources, regardless of the arrangement of the dividers.

In another exemplary aspect, the light indicators comprise light pipes which are placed into direct contact with the light sources when the liner is placed into the drawer. Each light pipe will rest upon a corresponding light source by force of gravity or other mechanical device, thereby insuring an adequate contact between each light indicator and light source.

In another exemplary aspect, the light pipes comprise elongated columns of a light transmitting material, and the light sources comprise LEDs. when the light pipes are placed into contact with the actuated LEDs, collimated light is transmitted through the light pipes.

In yet another aspect, the liner includes an identification device having information regarding the arrangement of the dividers and the items stored in each bin. The cabinet further includes a reader for reading the information from the identification device upon placement of the liner into the drawer or in proximity to a scanning device. The reader then transfers this information to the processor so that the processor will know which light indicators to light when a caregiver selects an item. Alternatively, the identification device may comprise an identifier, label, title, serial number, or the like which uniquely identifies the particular drawer. With this arrangement, a separate database having information relating to the configuration of the bins, the items stored therein, and the associated identifier will be provided. This information may be supplied to the processor (usually via a network from a host computer) so that when the dispensing unit reads the identifier on the identification device it will know the configuration of the bins and the items stored therein.

In still another aspect, drawer locks are provided within the cabinet to lock the drawers until receiving a signal from the processor. Each drawer may also include a visual indicator so that when an item is selected from the list of items, the visual indicator on the drawer having the selected item will be actuated. In yet another aspect, a sensor may be provided to detect if one of the drawers is retracted from the cabinet.

The invention further provides an exemplary method for dispensing items from a dispensing unit having a plurality of retractable drawers which are divided with dividers to form a plurality of bins for holding the items. According the method, item identification information is entered into the dispensing unit to select a desired type of item. One of the drawers having the selected item is withdrawn, and at least one light indicator which is adjacent to the bin having the selected item is lighted. Having been guided to the correct bin, a caregiver then removes the desired quantity of the selected type of item from the lighted bin.

In an alternative aspect, at least two light indicators may be lighted (preferably on opposite sides of the bin) to uniquely identify the correct bin. In one particular aspect, user and/or patient identification information are entered into the dispensing unit before selecting the item. In another aspect, a visual indicator is actuated on the drawer having the selected item to guide the caregiver to the correct drawer.

In one alternative aspect, the caregiver enters into the dispensing unit the quantity of items that have been removed from the bin. After entering this information, the drawer is closed. In the event that such information is not entered, the dispensing unit produces a record of the discrepancy. Optionally, an alarm or message may be provided to alert the caregiver of the discrepancy.

In still another aspect, the liner is periodically removed and replaced with another liner having a full inventory of items. The replacement liner may have a bin arrangement and/or inventory of items that are the same or different from the first liner. The dispensing unit is configured to detect the arrangement of the bins and the items within each bin so that when another item is selected from the list of items, at least one light indicator which is adjacent to the bin having the selected item will be lighted.

The dispensing unit may detect the configuration of the bins and the items within the bins in a variety of ways. For example, an identification device may be included on the drawer which includes the configuration and item information. This may then be directly read into the processor. Alternatively, the identification device may be a label (such as a serial number) which uniquely identifies the particular drawer. With this arrangement, a separate database having information relating to the configuration of the bins and the items stored therein will be provided. This information may be supplied to the processor (usually via a network from a host computer) so that when the dispensing unit reads the label on the identification device it will know the configuration of the bins and the items stored therein.

The invention still further provides an exemplary method for stocking items into drawers of a dispensing unit. According to the method, a liner is provided having a plurality of adjustable dividers. The dividers are arranged within the liner to form a preselected arrangement of bins. Different types of items are placed into the bins, and an identification device is attached to the liner which includes information identifying the arrangement of the dividers and the types of items held in the bins. The liner is then placed into the drawer, with the drawer including a reader which reads the information from the identification device. In this manner, the dispensing unit will know the specific configuration of the bins and which items are held in each of the bins. With this arrangement, the liner may be removed from the drawer after various items have been dispensed and replaced with a second liner having the same and/or a different arrangement of bins.

BRIEF DESCRIPTION OF THE DRAWINGS

FIG. 7 is a cross-sectional side view of cone of the drawers of the dispensing unit of FIG. 1.

FIG. 8 is a cross-sectional side view of a portion of the drawer of FIG. 7 taken along lines 8—8.

DESCRIPTION OF THE PREFERRED EMBODIMENT

Figure 1:
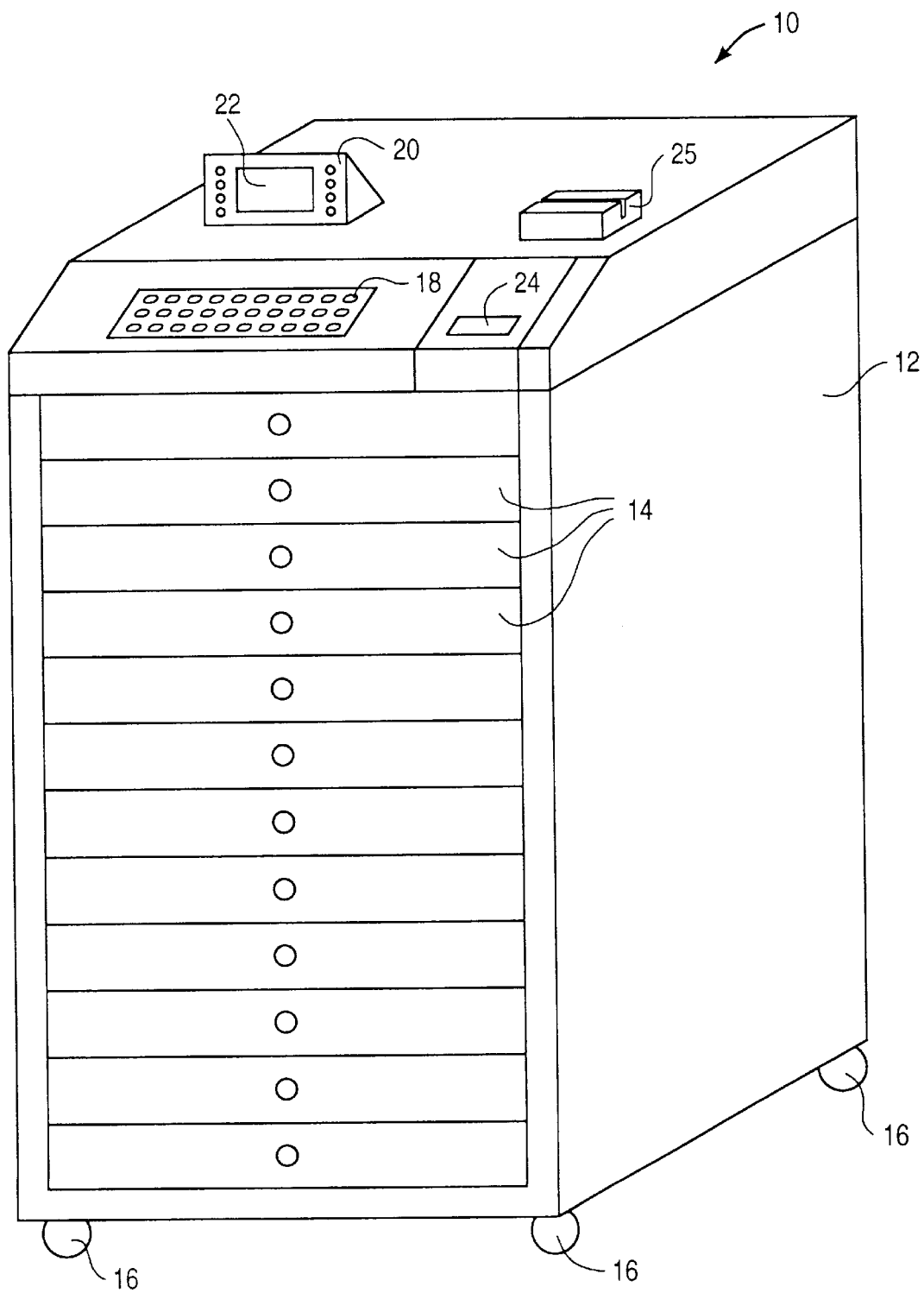
FIG. 1 is perspective view of an exemplary dispensing unit according to the present invention.

The invention provides an exemplary dispensing unit and methods for dispensing various items and for periodically restocking the items into the dispensing unit. Although useful in dispensing a wide variety of items, the invention will find its greatest use in medical facility environments where various medical supplies and pharmaceuticals are dispensed. The dispensing unit of the invention is related in some aspects to the dispensing device described in co-pending application Ser. No. 08/544,379, filed Oct. 10, 1995, the complete disclosure of which is herein incorporated by reference.

One particular feature of the dispensing unit of the invention is its ability to assist the caregiver in locating a selected item and ensuring accuracy in the process of taking the item. This is best accomplished by uniquely lighting at least a portion of a bin having the selected item so that the caregiver can quickly identify the location of the item. Such a lighting system may be employed with a variety of dispensing unit configurations, including those where the items are held in drawers, shelves, racks, and the like. The lighting system will be particularly useful in flexible storage location arrangements where the number and size of the individual bins which hold the items may be varied.

In one particular aspect, the dispensing unit of the invention will preferably comprise a cabinet having a plurality of retractable drawers. The drawers provide security to the items held therein by remaining locked to the cabinet until certain information is entered into a processor. In this way, the medical facility can control access to the items by configuring the dispensing unit to allow access to its drawers only when the requisite information has been entered. Such information can include, for example, patient identification information, caregiver identification information and password, item identification information and the like.

The dispensing unit of the invention is configured to optimize the storage space within each of its drawers. Such optimization is provided by including adjustable dividers which are employed to create customized bins to accommodate different sized items. In this manner, the space within each drawer is more fully utilized. The drawers will also preferably be configured so that they can fit within a cabinet having dimensions which are generally accepted by the health care industry. The height of each drawer may also be varied to optimize the space within the cabinet. For example, each drawer may be designed to have a height that is either two inches or four inches so that the cabinet can uniformly be filled with different sized drawers.

Another feature of the dispensing unit of the invention is the use of removable drawer liners. This arrangement allows a liner having a depleted inventory to be quickly exchanged with a new liner having a full inventory of items, including current expiration dates for any medications. With this arrangement, the liners may be refilled from a central inventory or pharmacy area rather than in the hall where caregivers may need to access the dispensing unit. Additionally, the liners may be constructed from relatively inexpensive materials, such as plastics, so that the liners may be discarded after use or recycled. In turn, this greatly reduces the cost to the health care facility.

Still another feature is that each liner may have an identification device included thereon which is readable by the dispensing unit so the dispensing unit will know the specific configuration of bins and items held therein when placed into each drawer.

Referring now to the figures, an exemplary dispensing unit 10 will be described. As shown in FIG. 1, dispensing unit 10 comprises a cabinet 12 having a plurality of retractable drawers 14. Although shown with 12 drawers, the number of drawers may be varied. For example, in one preferable configuration, cabinet 12 will include 13 or 14 drawers. Conveniently, cabinet 12 rests upon a plurality of wheels 16 which allows the dispensing unit 10 to be wheeled throughout the health care facility. Although cabinet 12 may be fashioned with various dimensions, a preferable size will be about 26 inches wide and 23 inches deep.

Dispensing unit 10 further includes a processor (hidden within cabinet 12) and a keyboard 18 for entering various information into the processor. For example, keyboard 18 may be employed to enter patient identification information, caregiver identification information, requests for item removal, and the like into the processor. Optionally, dispensing unit 10 may further include a second entry device 20 which is connected to the processor and includes a screen 22 which allows the caregiver to scroll through various lists of information in order to select a highlighted item. For example, a caregiver may scroll through a list of patient names or item names in order to select a certain patient or to enter an item removal request. Conveniently, a printer 24 is provided on cabinet 12 to print various reports generated by the processor.

optionally, cabinet 12 may further include a mag or bar code reader 25 which is connected to the processor. Reader 25 may be provided to allow a user or a patient to be conveniently identified by swiping an appropriate ID card through reader 25. Reader 25 may also be employed to read an identification device associated with the drawers as described in greater detail hereinafter.

Figure 2:
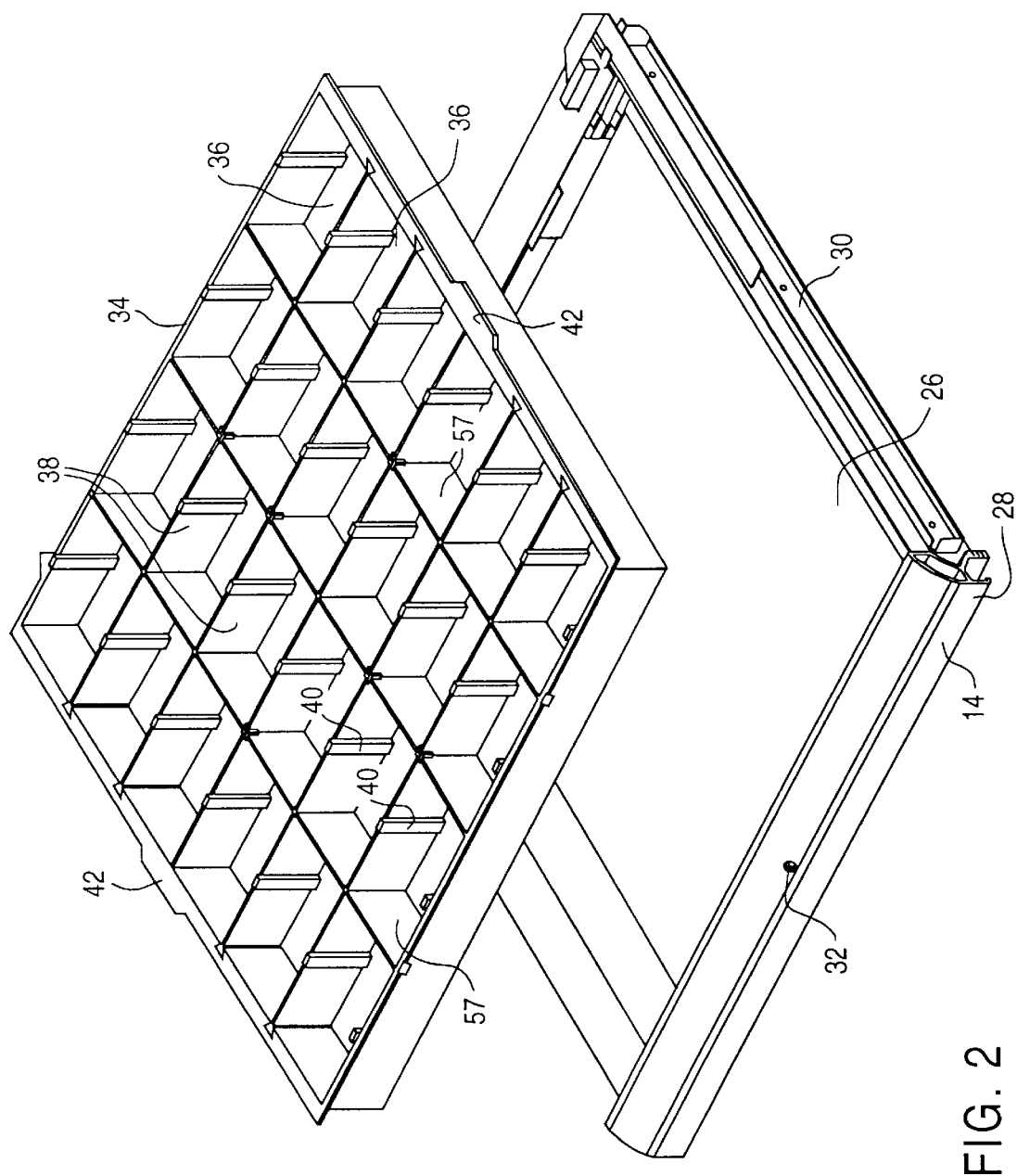
FIG. 2 is a perspective view of a drawer of the dispensing unit of FIG. 1 having a removable liner according to the invention.

Referring now to FIG. 2, one of drawers 14 will be described in greater detail. Drawer 14 comprises a frame 26 having a handle 28 and a track 30 which allows the tray to be slid in an out of cabinet 12 (FIG. 1). A visual indicator 32, such as an LED, is provided on drawer 14 to allow a specific drawer to be identified upon entering an item removal request as described in greater detail hereinafter. Drawer 14 is configured to receive a removable liner 34 which holds the items to be dispensed. Liner 34 is divided into a plurality of bins 36 by a plurality of adjustable transverse dividers 38 and longitudinal dividers 57. Attached to at least some of the dividers are light pipes 40 which are employed to guide a caregiver to a specific bin as described in greater detail hereinafter. Liner 34 is configured to conveniently rest within the frame 26 and may be removed by simply lifting liner from drawer 14 by handles 42.

Figure 3:
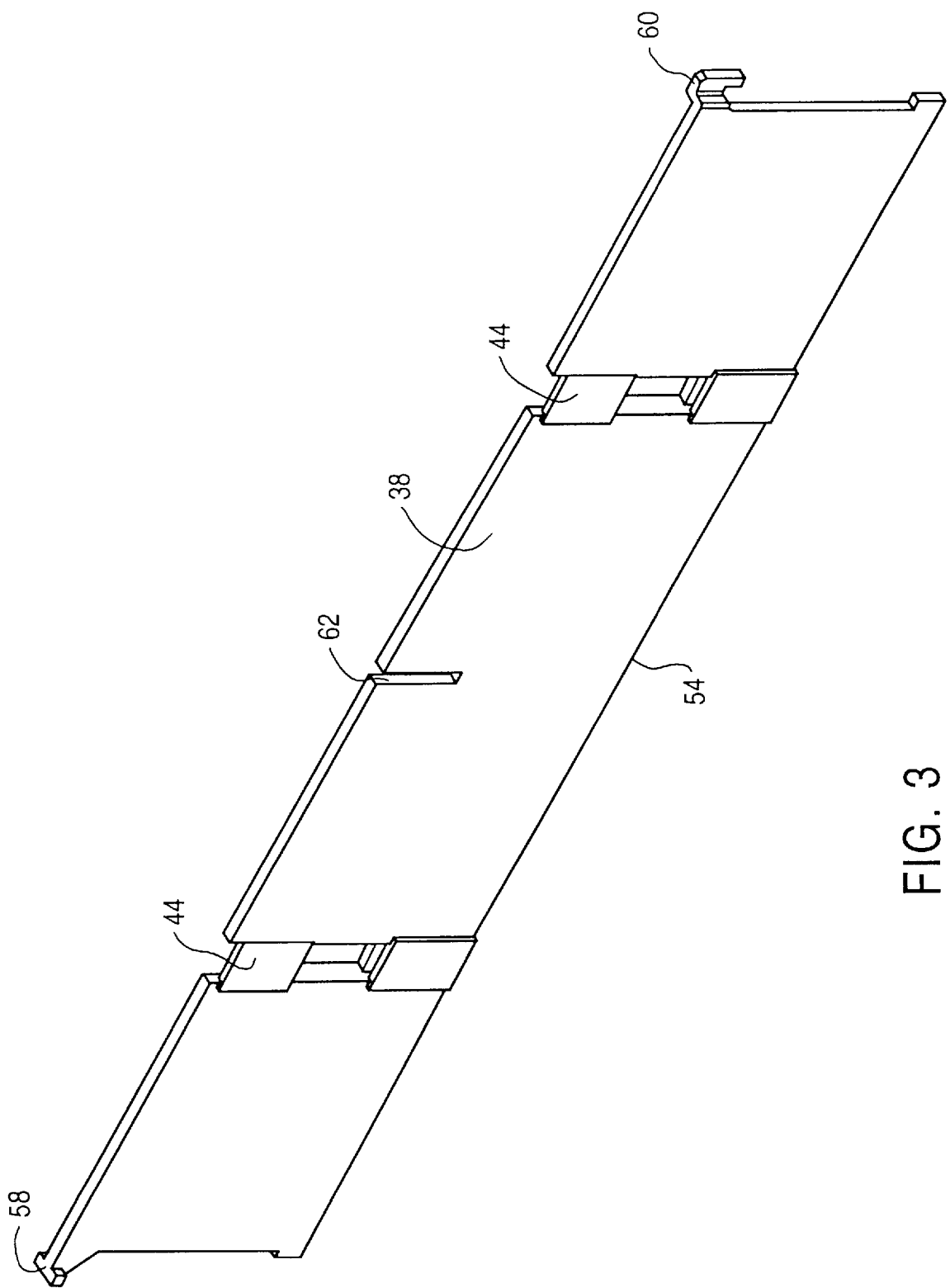
FIG. 3 is a perspective view of a transverse adjustable divider of the liner of FIG. 2.
Figure 4:
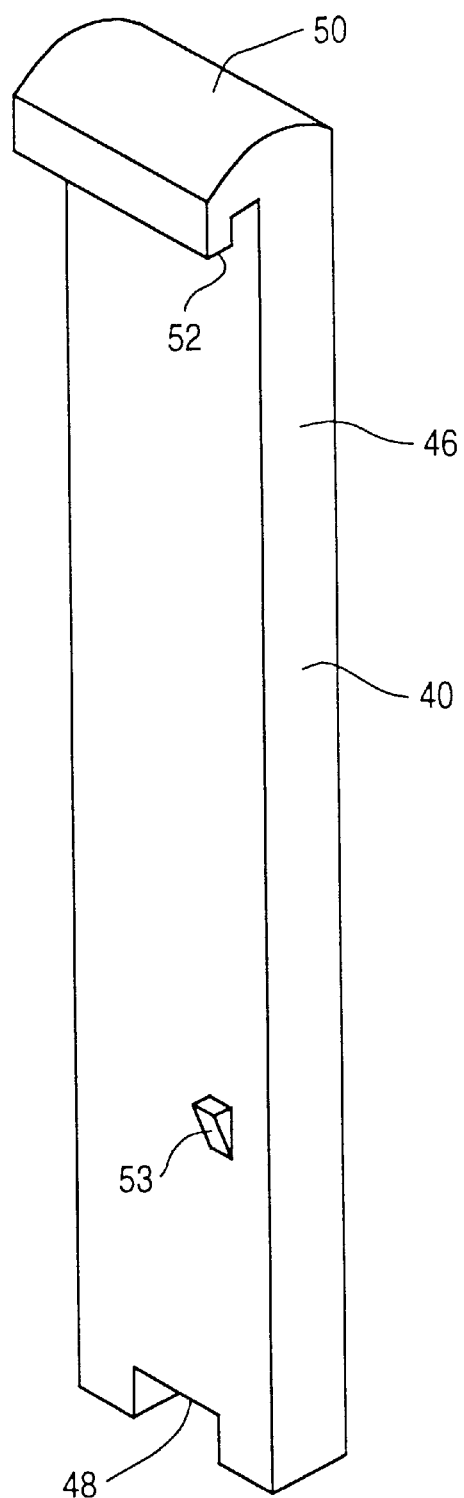
FIG. 4 is a perspective view of a light pipe that is attachable to the divider of FIG. 3.

Referring also now to FIGS. 3 and 4, construction of a transverse divider 38 to facilitate attachment of light pipes 40 will be described. As shown, divider 38 includes a pair of receiving regions 44 to which light pipes may be attached. Although shown with two receiving regions 44 it will be appreciated that additional numbers of regions may be provided depending upon the particular length of the divider or on the desired number of light pipes per bin. As shown in FIG. 4, light pipe 40 comprises an elongate body 46 having a recessed region 48, a top region 50 and a lip 52 at the top region 50. Light pipe 40 is attached to divider 38 by inserting lip 52 over receiving region 44 where light pipe 40 will rest on divider 38 by force of gravity or by a lock tab 53. Body 46 of light pipe 40 has a length which is longer than the height of divider 38 so that recessed region 48 will be below a bottom end 54 of divider 38. This allows recessed region 48 to extend below liner 34 so that it may engage a light source within drawer 14 as described in greater detail hereinafter. Further, recessed region 48 will preferably comprise a flat surface for interacting with the light sources as described in greater detail hereinafter. Light pipe 40 will preferably be constructed of a light transmitting material, such as acrylic, which will allow collimated light to pass through body 46 to illuminate top region 50. In this way, top region 50 may be brightly illuminated with a relatively small light source.

Figure 5:
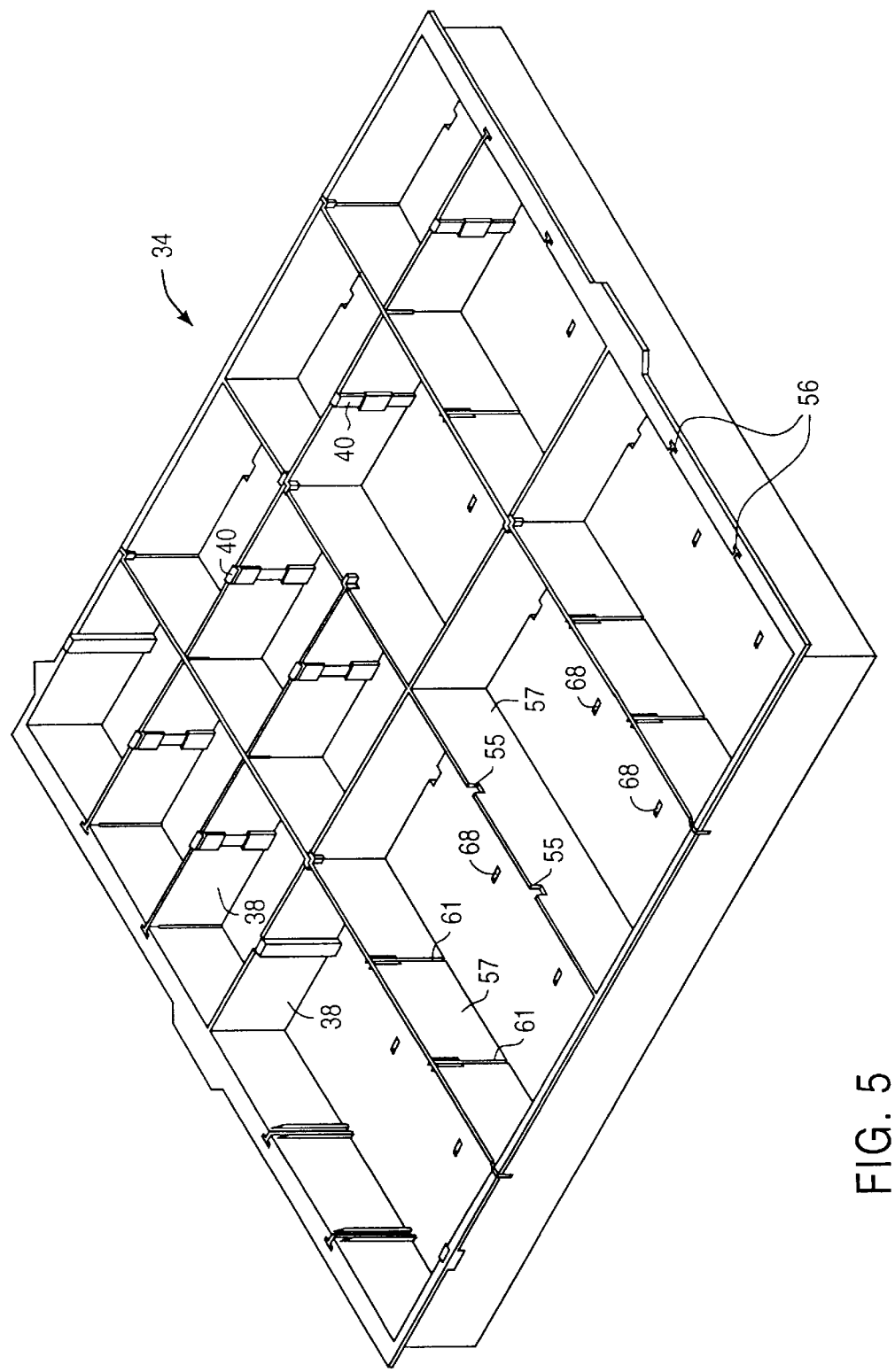
FIG. 5 is a perspective view of a removable liner of the dispensing unit of FIG. 1 having an alternative arrangement of bins which is made possible by the adjustable dividers according to the invention.
Figure 6:
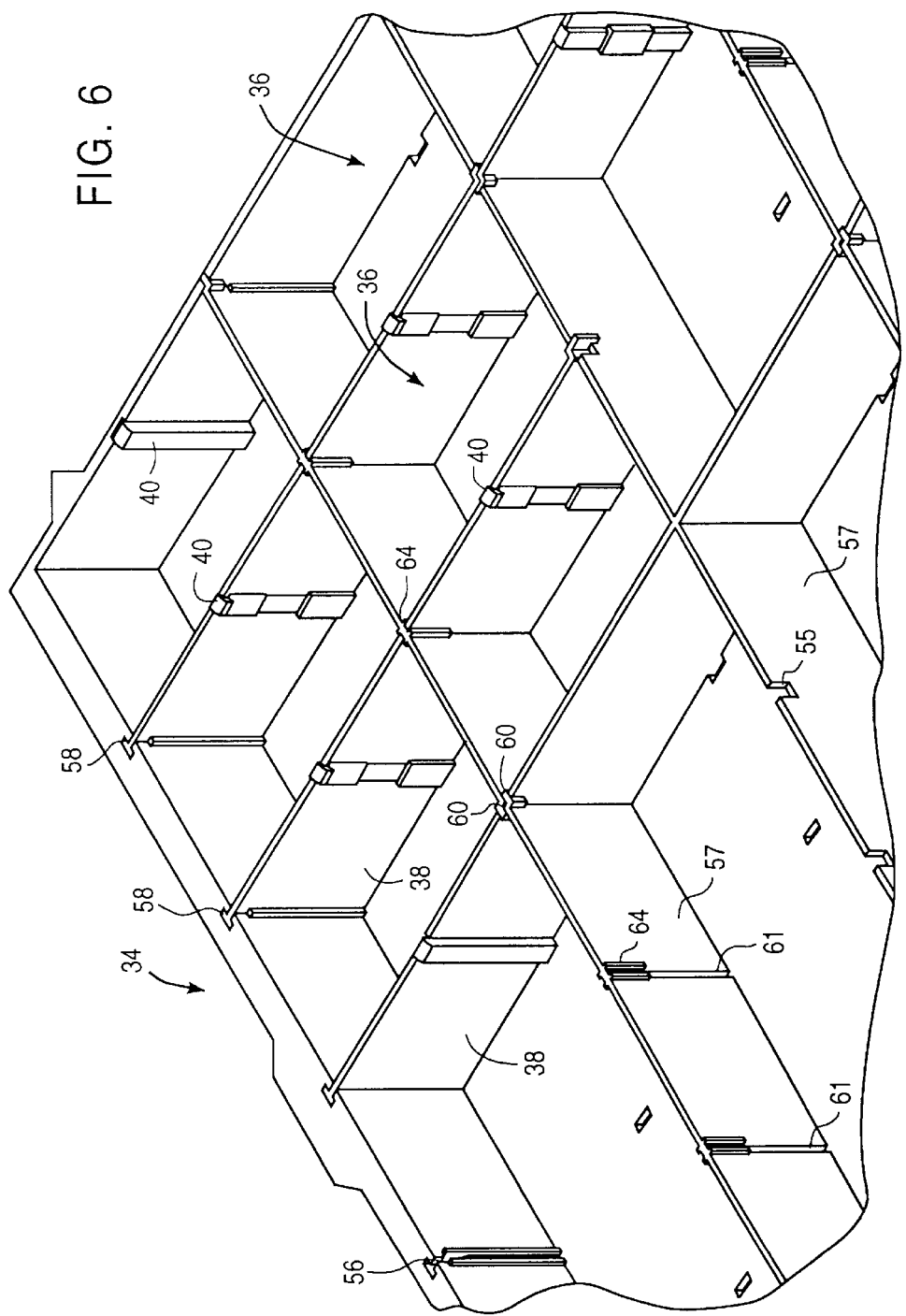
FIG. 6 is a more detailed view of the bin of FIG. 5.

As shown in FIG. 2, liner 34 is equally divided into a two dimensional array of bins. However, one particular advantage of employing dividers 38 is that the number and size of bins 36 may be tailored depending upon the particular items held within each bin. By way of illustration, one such arrangement is shown in FIGS. 5 and 6. To facilitate such an arrangement, liner 34 includes a plurality of elongated slots 56 into which the transverse dividers 38 (see FIG. 3) may be placed. More specifically, dividers 38 include a T-connector 58 at one end which is slid into slots 56 of liner 34. At the opposite end, divider 38 includes a Z-connector 60 which mates with a slot 55 of longitudinal divider 57. Some of longitudinal dividers 57 also include a slot 61 which is mated with one of slots 62 of divider 38 (see FIG. 3) to connect the dividers as shown in FIG. 6. Dividers 57 may also include a pair of tabs 64 to guide divider 57 over slot 62 when divider 57 is slid down divider 38. Hence, by providing various types of dividers, the dividers may be connected in various arrangements to form specific numbers of sizes of bins within liner 34.

Formed within liner 34 are a plurality of apertures 68 (FIG. 5) for receiving light pipes 40. Apertures 68 are sized to be large enough to allow light pipes 40 to pass through liner 34. Apertures 68 will preferably be arranged in a two dimensional array so that regardless of the configuration of dividers 38, an aperture 68 will be present for each light pipe 40.

In a preferred arrangement, at least two light pipes 40 which are attached to separate dividers 38 (preferably opposite of each other) will be associated with each bin 36 having an item stored therein. This arrangement allows a specified bin to be uniquely identified, e.g., by surrounding the bin, upon the selection of an item by lighting the two light pipes. It will be appreciated that more than two light types could be provided for each bin 36 if desired.

Alternatively, a single light pipe may be employed to uniquely identify the specified bin. For example, the light pipe could be configured in the shape of an arrow or other pointer which points the user to the correct bin.

Referring now to FIGS. 7 and 8, the integration of light pipes 40 with a plurality of light sources 70 will be described. Light sources 70 preferably comprise LED's having a generally flat-topped surface onto which recessed regions 48 of light pipes 40 (see FIG. 4) are received when liner 34 is placed into drawer 14. Hence, when liner 34 is inserted into drawer 14, light pipes 40 extend through apertures 68 and directly contact light sources 70. In this manner, each light pipe 40 will rest on a corresponding light source 70 by force of gravity or by some mechanical device. For example, the light sources 70 could be upwardly biased so that they will press against light pipes 40 when liner 34 is placed into the drawer. With this arrangement, no lens is needed between light source 70 and light pipe 40 to collimate the light. Instead, the light from the light source remains collimated through each light pipe 40 so that the top regions 50 will brightly illuminate. In this way, a relatively small light source, such as an LED, may be employed.

Light sources 70 will preferably be arranged in a two dimensional array which corresponds to the location of apertures 68 in liner 34. In this manner, regardless of the arrangement of dividers 38 and light pipes 40, every light pipe 40 will rest on a corresponding light source 70. Light sources 70 will preferably be surface mounted to a flexible PC "board" 72, which will preferably comprise an insulated nylon sheet. PC "board" 72 is connected to the processor so that signals may be sent to light selected ones of the light sources 70 to uniquely identify the bin having the selected item. Use of such a PC "board" of mylar is advantageous because of its relatively thin size which provides more storage space within drawer 14. Preferably, PC "board" 72 will be 0.010 inches thick or less.

As shown in FIG. 7, drawer 14 further includes a second PC "board" 74 which is in electrical communication with a solenoid 76 to move a latch 78. In turn, latch 78 is employed to lock drawer 14 to cabinet 12. Electrical current is provided to PC "board" 74 through a line 80, while power is supplied to PC "board" 72 by a line 82.

Optionally, drawer 14 may include a sensor 84 which is employed to detect when drawer 14 is withdrawn from cabinet 12. Sensor 84 is connected to PC "board" 74 by a line 85. If a caregiver neglects to close drawer 14 after a transaction, sensor 84 will detect that the drawer is still open so that an alarm or reminder signal may be produced by the processor. An exemplary sensor will comprise an infrared source and receiver. With such a sensor, a vane will be employed to break the light path when the drawer opens.

Latch 78 will preferably unlock after appropriate information is entered into the processor by the caregiver. Such information can include for example, caregiver or patient identification information (including passwords) and item identification information. After a specified time period, latch 78 will again lock so that if the caregiver neglects to open the drawer, the drawer will relock. Hence, the drawer will be able to relock itself after a "time out" period has elapsed to prevent further access.

An exemplary method for dispensing items from dispensing unit 10 will now be described. Initially, a caregiver approaches dispensing unit 10 and enters user identification, and preferably also a private password using keyboard 18 or entry device 20. The caregiver then identifies the patient requiring a supply or medication. This is also entered into the processor using keyboard 18 or entry device 20. The caregiver then selects the desired supply or medication. This may be done by entering the name into keyboard 18, by scrolling through a list of items on screen 22, or by swiping an ID card through reader 25. Preferably, the caregiver will also enter the number of items of the selected type that are to be removed.

Upon selection, the processor will send a signal to light the visual indicator 32 on the specific drawer having the requested item. The processor will also send a signal to unlatch latch 78 so that drawer 14 may be withdrawn from cabinet 12. Alternatively, the drawer may include a switch which is accessible to the caregiver and which may be pressed by the caregiver to open the solenoid lock. The caregiver then retracts the proper drawer and will be led by at least one lighted light pipe 40 to the correct bin. More preferably, at least two light pipes 40 will be lighted to guide the user to the correct bin. For example, light pipes 40 on two opposing dividers 38 may be lighted. Alternatively, light pipes provided on adjacent dividers may be lighted. Upon location of the lighted bin, the caregiver then removes the requested item (or a plurality of items of the same type) from the lighted bin.

At this point, the method provides the optional step of verifying the count of specific item taken. This is done by prompting the caregiver to enter into the processor via keyboard 18 or entry device 20 the number of items of the specific type that were removed and the number remaining. If the caregiver closes drawer 14 before verifying the count, the processor may produce an error message and/or produce an alarm. A record of this event will also preferably be maintained within the processor.

The invention further provides an exemplary method for restocking items into dispensing unit 10. Restocking is facilitated by use of removable liners 34. In particular, to restock a specific drawer, the drawer is opened and liner 34 is removed by simply lifting handles 42 and removing liner 34 from the drawer. Another liner having a full stock of inventory is then placed into the drawer.

The replacement liner may be configured to have the same arrangement of bins and items or a different arrangement of bins and items. The liner will preferably include an identification device which will allow the processor to identify the specific arrangement of bins and items held in the bins when certain information is transferred to the processor from the identification device by a reader on the drawer or the cabinet. For example, the identification device may comprises a smart or proximity chip, such as those commercially available from Racom Systems, Inc., Englewood, Colo. which includes information regarding the configuration of the bins and/or the types of items in the bins. With the configuration, the configuration and item information is transferred directly from the identification device to the processor.

Alternatively, the identification device may comprise an identifier, such as a label or a serial number bar code, that simply identifies the particular liner. This information is transferred by the reader to the processor which will then know the specific liner which has been placed into the cabinet. Preferably, only one drawer will be opened at a time so that the processor will know which drawer has received the liner. The processor further includes a database which includes information on the particular configuration of each liner, the items stored in each bin, and an associated serial number. This information will preferably be entered into a host computer at the time of filling by the supplier and then transferred to the processor via a network. Hence, when the reader reads the serial number from the liner, the processor will be able to look up the information on the bin configuration and the items stored in the bins. This information may then be updated within the processor when items are removed from or returned to the bins.

By configuring the liner in this manner, the liner may be restocked at a remote location so that time is saved and accuracy is assured when replacing the liner. Further, by employing the identification device, the liner can be adjusted to have any arrangement of bins and items. As previously described, the light sources 70 will be arranged such that each bin may be appropriately lighted when an item is selected, regardless of the bin configuration.

The invention has now been described in detail for purposes of clarity and understanding. However, it will be appreciated that certain changes and modifications may be made within the scope of the invention. Therefore, the above description should not be taken as limiting the scope of the invention, instead, the scope of the invention should be determined with reference to the appended claims, along with the full scope of equivalents to which those claims are entitled.

What is claimed is:

1. A dispensing system, comprising:
    a cabinet having at least one storage location;
    a plurality of dividers which divide at least a portion of the storage location into a plurality of bins for holding items, wherein at least some of the dividers are adjustable to provide for multiple possible bin arrangements;
    a processor having a memory for storing a list of items which are held within the bins and an entry device for entering requests for item removal; and
    a plurality of light indicators attached to at least some of the dividers, wherein the light indicators are arranged such that at least one light indicator uniquely identifies one of the bins when lighted, wherein the storage location further includes a plurality of light sources which are in communication with the processor and which provide light to the light indicators, wherein for every possible bin arrangement in said portion of said storage location there is at least one light source and one corresponding light indicator, wherein the processor further includes information relating to the arrangement of the dividers, and wherein selection of one of the items from the list of items causes the processor to send a signal to actuate at least one of the light sources which are associated with the bin having the selected item.

2. A The system of claim 1, wherein the storage location includes a plurality of connecting points which are arranged such that the dividers will form orthogonal bins when connected to the connecting points, and wherein the light sources are arranged in a two dimensional array such that at least two light indicators are always aligned with at least two light sources for each bin.

3. The system of claim 1, wherein the light indicators comprise light pipes which are placed into direct contact with the light sources when the dividers are placed into the storage location.

4. The system of claim 3, wherein the light pipes comprise elongate columns of a light transmitting material.

5. The system of claim 3, wherein the light sources comprise LEDs.

6. The system of claim 1, wherein the storage location comprises a frame and a removable liner to which the dividers are removably attached, and wherein the light sources are fixedly attached to the frame so that placement of the tray onto the frame places the light indicators in alignment with the light sources.

7. The system of claim 6, wherein the liner includes an identification device having information regarding the arrangement of the dividers and the items stored in each bin, wherein the storage location further includes a reader for reading the information from the identification device upon placement of the liner onto the frame and transferring the information to the processor.

8. The system of claim 1, wherein the storage location comprises a retractable drawer.

9. The system of claim 8, further comprising a drawer lock within the cabinet which locks the drawer until receiving a signal from the processor.

10. The system of claim 8, further comprising a plurality of retractable drawers, each having a visual indicator located thereon, wherein the selection of an item from the list of items actuates the visual indicator on the drawer having the selected item.

11. The system of claim 10, further comprising a sensor to detect if one of the drawers is retracted from the cabinet.

12. The system of claim 1, wherein the light indicator comprises an arrow.

13. A dispensing unit, comprising:
    a cabinet having a plurality of drawers, wherein a plurality of light sources are attached to a bottom of each of the drawers;
    a liner removably held within each of the drawers above the light sources;
    a plurality of adjustable dividers which divides at least a portion of the liner into a plurality of bins for holding items, wherein at least some of the dividers are adjustable to provide for multiple possible bin arrangements;

a processor having a memory for storing a list of items which are held within the bins and an entry device for entering requests for item removal; and a plurality of light indicators which are attached to the dividers, wherein the light indicators are arranged such that each light indicator is aligned with a corresponding light source, wherein the light sources are in communication with the processor, wherein for every possible bin arrangement in said portion of said liner there is at least one light source and one corresponding light indicator, wherein the processor further includes information relating to the arrangement of the dividers, and wherein selection of one of the items from the list of items causes the processor to send a signal to actuate at least one of the light sources which are associated with the bin having the selected item.

14. The dispensing unit of claim 13, wherein the light indicators are arranged such that at least two of the light indicators are associated with each bin.

15. The dispensing unit of claim 13, wherein the light indicators are in direct contact with the light sources when the liner is placed into the drawer.

16. The dispensing unit of claim 13, wherein the drawers have a height that is either two inches or four inches.

17. The system of claim 13, wherein the light indicators comprise light pipes which are each constructed of an elongate column of a light transmitting material.

18. The system of claim, 13, wherein the light sources comprise LEDs.

19. A method for dispensing items from a dispensing unit having a plurality of retractable drawers which are divided with dividers to form a plurality of bins for holding the items, wherein at least one of the drawers includes a plurality of light sources, the method comprising:

adjusting at least some of the dividers in the drawer having the light sources to form a preferred arrangement of the bins;

providing the dispensing unit with information on the preferred arrangement;

entering item identification information into the dispensing unit to select a desired type of item from one of the bins having the preferred arrangement;

withdrawing the drawer having the selected item;

lighting at least one of the light sources to light at least one light indicator which is attached to at least one of the dividers which forms the bin having the selected item; and removing a desired quantity of the selected type of item from the bin.

20. The method of claim 19, further comprising entering user and patient identification information in the dispensing unit before selecting the item.

21. The method of claim 19, further comprising actuating a visual indicator on the drawer having the selected item.

22. The method of claim 19, further comprising entering into the dispensing unit the quantity of items removed from the bin.

23. The method of claim 22, further comprising closing the drawer after removing the desired quantity and making a discrepancy record if the quantity of items removed was not previously entered.

24. The method of claim 19, wherein the dividers are coupled to a liner, and further comprising removing the liner and replacing the liner with a second liner having a full inventory of items.

25. The method of claim 24, wherein the second liner has a bin arrangement which is different that the arrangement of the first liner, and further comprising selecting an item from the list of items and lighting at least two light indicators which are adjacent the bin having the selected item.

26. A dispensing system, comprising:

a cabinet having at least one storage location;

a plurality of dividers at least some of which are adjustable to provide for multiple possible bin arrangements, wherein the dividers divide at least a portion of the storage location into a plurality of bins for holding items;

a processor having a memory for storing a list of items which are held within the bins and an entry device for entering requests for item removal; and means attached to at least one of the dividers and connected to the processor to light at least a portion of one of the bins to guide a user to a selected item such that selection of one of the items from the list of items causes the processor to send a signal to the lighting means to cause the portion of the bin having the item to be lighted regardless of the particular bin arrangement.

27. A dispensing system, comprising:

a cabinet having at least one storage location;

a plurality of adjustable dividers which divide the storage location into a plurality of bins for holding items;

a processor having a memory for storing a list of items which are held within the bins and an entry device for entering requests for item removal; and a plurality of light indicators operably attached to at least some of the dividers, wherein the light indicators are arranged such that at least one light indicator uniquely identifies one of the bins when lighted;

wherein the storage location further includes a plurality of light sources which are in communication with the processor and which provide light to the light indicators, wherein the storage location comprises a frame and a removable liner to which the dividers are removably attached, and wherein the light sources are fixedly attached to the frame so that placement of the tray onto the frame places the light indicators in alignment with the light sources.

* * * * *